United States Patent [19]
Watanabe et al.

[11] Patent Number: 5,209,239
[45] Date of Patent: May 11, 1993

[54] APPARATUS FOR CYSTOGRAPHIC INSPECTION

[75] Inventors: Hideki Watanabe, Aichi; Takashi Kojima; Masaru Maruyama, both of Nagano, all of Japan

[73] Assignee: Hakko Electric Machine Works Co., Ltd., Nagano, Japan

[21] Appl. No.: 525,554

[22] Filed: May 18, 1990

[30] Foreign Application Priority Data

Apr. 9, 1990 [JP] Japan .................................. 2-93538

[51] Int. Cl.$^5$ ........................ A61B 5/103; A61B 6/00
[52] U.S. Cl. ..................................... 128/774; 128/656
[58] Field of Search ............... 128/774, 658, 656, 654; 606/1

[56] References Cited

U.S. PATENT DOCUMENTS

| | | |
|---|---|---|
| 3,529,633 | 9/1970 | Vaillancourt . |
| 3,908,635 | 9/1975 | Viek .................................... 128/768 |
| 4,111,190 | 9/1978 | Plumridge ............................ 128/658 |
| 4,281,211 | 7/1981 | Tatum et al. . |
| 4,294,260 | 10/1981 | Veatch ................................. 128/654 |
| 4,477,693 | 10/1984 | Krabec et al. . |
| 4,571,240 | 2/1986 | Samson et al. ....................... 604/96 |
| 4,791,236 | 12/1988 | Klein et al. . |
| 4,867,742 | 9/1989 | Calderon .............................. 604/28 |
| 5,034,009 | 7/1991 | Mouchel ............................... 606/1 |

FOREIGN PATENT DOCUMENTS

| | | |
|---|---|---|
| 3447642 | 9/1986 | Fed. Rep. of Germany . |
| 1582808 | 1/1981 | United Kingdom . |
| 2155686 | 9/1985 | United Kingdom . |
| 2201829 | 9/1988 | United Kingdom . |

Primary Examiner—Lee S. Cohen
Assistant Examiner—Kevin Pontius
Attorney, Agent, or Firm—Helfgott & Karas

[57] ABSTRACT

An apparatus for cystographic inspection used for observing and measuring the urethrophaxis portion and posterourethovesical angle of a patient of the acraturesis caused by a ventral pressure, comprises a catheter, in the housing of which a flexible urethral locus indicating member, provided with a marking member, is positioned. The flexed condition of the urethral and the posterourethrovesical angle can be clearly confirmed by the urethral locus indicating member, and the position of an exterior urethral opening member, and position of an exterior urethral opening can be surely grasped by the marking member which can be roentgenographed and which is positioned on the urethral locus indicating member and that it is prevented from penetrating into the uretra and this assists in examining of the external urethral opening during roentgenography of the urethral locus indicating member of the catheter.

8 Claims, 2 Drawing Sheets

APPARATUS FOR CYSTOGRAPHIC INSPECTION

FIELD OF THE INVENTION

The present invention relates to a medical inspection apparatus, and more particularly to an apparatus for cystographic inspection used for observing and measuring the urethrophraxis portion and posterourethrovesical angle of a patient of the acraturesis caused by a ventral pressure.

BACKGROUND OF THE INVENTION

In order to observe the flexed state of the urethra and the posterourethrovesical angle in such a patient of the acraturesis caused by a ventral pressure and the like, a cystographic inspection by which such urethral portions are roentgenographed is indispensable in the present medical art.

In such conventional cystographic inspection, the flexed and abstructed states of the urethra have been examined by filling a contrast medium into a catheter, inserting the contrast medium filled catheter into the urethra of the patient so as to protrude a painted end of the catheter into the urinary bladder and taking a roentgenograph in such a situation.

However, in such a conventional system, the catheter tends to bend at the curved and abstructed portion of the urethra and thus, the roentgenograph of this portion shows an unclear image. Further, the position of the external urethral opening can not clearly be indicated in the roentgenograph, and the mutual angle and positional relationships of such individual organs in a roentgenogram become obscure. Therefore, it is very difficult to achieve a precise cystographic inspection.

It is therefore an object of the present invention to provide an apparatus for cystographic inspection which can achieve a precise cystographic examination.

SUMMARY OF THE INVENTION

According to the present invention, there is provided an apparatus for cystographic inspection, comprising a catheter which can be inserted from the urethra into the urinary bladder, can inject a contrast medium into the urinary bladder and can be drawn out of the urethra after the injection of the contrast medium; a urethral locus indicating member which is formed in the form of a flexible chain or string, previously loaded into the catheter and of which image can be taken by roentgenography, is emitted into the urinary bladder from its front portion upon the injection of the contrast medium into the urinary bladder with the catheter and is left in the region extending from the urethra into the urinary bladder after the catheter is drawn out of the urethra; and a marking member which can be roentgenographed, has a diameter larger than that of the urethral locus indicating member and is disposed in the vicinity of the external urethral opening after the catheter is drawn out of the urethra.

According to the present invention, a catheter is drawn out of the urethra after injecting a contrast medium into the urinary bladder by the catheter, and an urethral locus indicating member which can be roentgenographed and is flexible, is left in the region extending from the exterior urethral opening into the urinary bladder, so that an image or roentgenograph of the urethral locus indicating member can be clearly observed along the entire region extending from the exterior urethral opening into the urinary bladder. Consequently, the flexed condition of the urethra and the posterourethrovesical angle can be clearly measured.

Further, a marking member along with the urethral locus medicating member is disposed by the exterior urethral opening, so that the position of the exterior urethral opening can be surely grasped by the marking member, and consequently, the mutual angle and positional relationships of such individual organs in the roentgeogram can be clearly observed.

BRIEF DESCRIPTION OF THE DRAWINGS

The foregoing and other objects, aspects and advantages of the invention will be better understood from the following detailed description of a preferred embodiment of the invention with reference to the drawings, in which.

DESCRIPTION OF PREFERRED EMBODIMENTS

Referring to appended drawings, a preferred embodiment of the present invention will be described in detail below.

Figure 1:
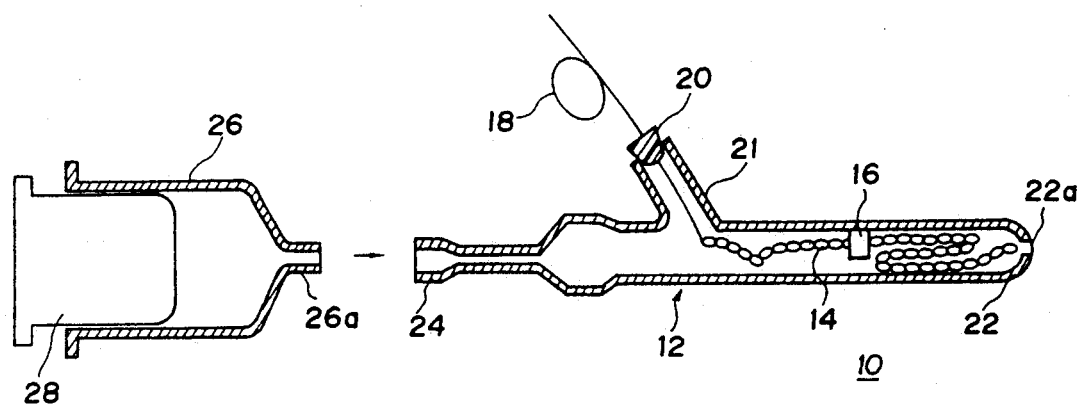
FIG. 1 is sectional view of a preferred embodiment of the apparatus used for cystographic inspection according to the invention.

FIG. 1 shows the entire construction of an apparatus used for cystographic examination of the present invention. This apparatus 10 used for cystographic examination comprises a catheter 12 to be inserted into the urethra of a patient, a chain 14 loaded in the catheter 12, a marker 16 mounted on a portion of the chain 14, a string 18 connected to one end of the chain 14 and a rubber cap 20 to support the string 18.

The catheter 12 is used for injecting a contrast medium into the urinary bladder. This catheter 12 is inserted into the urethra and the urinary bladder upon the injection of the contrast medium to be inserted into the bladder, and it is pulled out of the urethra upon roentgenographing after the injection of the contrast medium into the bladder. The catheter 12 comprises a TEFLON ® tube having a length of about 11 cm and has a branched tube 21 formed in its intermediate portion. The catheter 12 has one end (on the right end of FIG. 1) formed round in such a way that it can be smoothly inserted into the urethra, and has a thin film 22a sticked on the surface of the utmost end 22 thereof. On the other hand, other left end 24 of the catheter 12 is formed in such a way that a pointed end 26a of a syringe cylinder 26 constituting an injector to inject a contrast medium into the urinary bladder can be fitted into the other left end 24 of the catheter 12. Into this cylinder 26 is slidably engaged a piston 28, as well known.

The chain 14 is utilized to indicate the bending state of the urethra extending from an exterior urethral opening to the urinary bladder. The chain 14 is made of a nickel plated brass (an acid-proof metal), has the length of about 30–40 cm and is loaded in the catheter 12 prior to the cystographic examination. When a contrast medium is injected into the catheter 12, the chain 14 along with the contrast medium is emitted into the urinary bladder while breaking the thin film 22a sticked on the surface of the utmost end of the catheter 12. The chain 14 is left throughout the area exending from the urethra to the urinary bladder even after the catheter 12 was pulled out of the urethra.

A marker 16 is utilized to indicate the position of the exterior urethral opening. The marker 16 is preset in the predetermined position of the chain 14 in such a way that the marker 16 is not penetrated into the urethra when the chain 14 is emitted into the urinary bladder.

Figure 2:
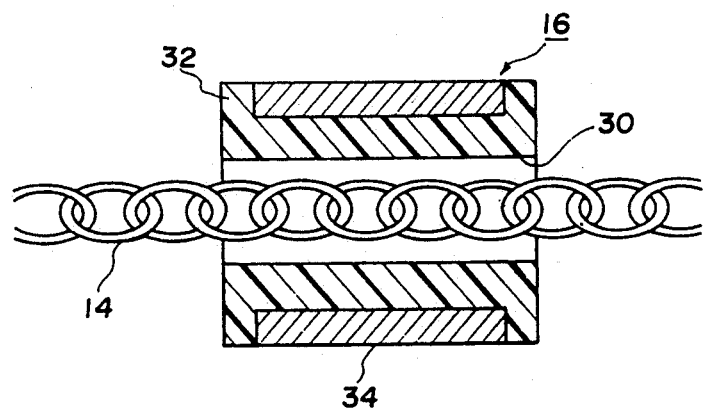
FIG. 2 is an enlarged sectional view of one of the main components in the apparatus shown in FIG. 1.

FIG. 2 shows the inner structure of the marker 16. As shown in FIG. 2, the cylindracal marker 16 has an opening 30 formed in the core thereof and the chain 14 is passed through the opening 30. The marker 16 can slidably be moved on the chain 14, and thus the marker 16 can be disposed or fixed in the desired position of the chain 14. The inner portion of the marker 16 is made of a gummous plastic material has a cylindrical shape with flanges on its opposite ends. A contrast medium is mixed into the gummous plastic material for roentgenography. Onto the periphery of the marker 16 is provided a metal ring 34 of a material such as stainless steel and the like by suitable means such as welding with a pressure or fitting process.

The string 18 is utilized to draw the chain 14 out of the urethra 44 after the completion of the roentgenography and in general, No. 1 thread of NYLON ® is used as the string 18. The opposite end of the string 18 is pulled out from a rubber cap 20 through the branched tube 21.

The rubber cap 20 is used to prevent the string 18 from intrudding into the urethra without resistance and holds the string 18 in situ by the elastic force of the rubber.

Referring to FIGS. 3A to 3D, a preferred method to operate such an apparatus used for cystographic examination and its functions will be described hereinafter.

Figure 3A:
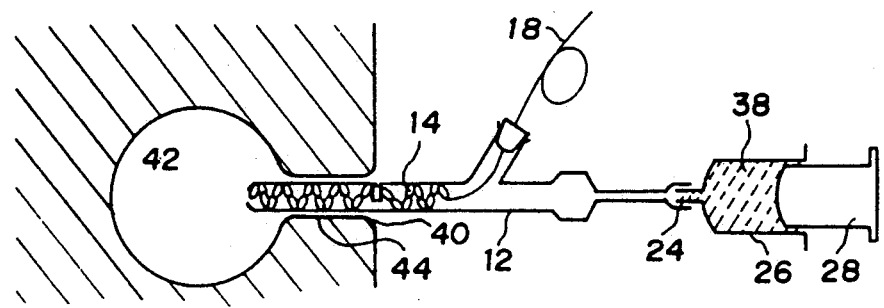
FIGS. 3A to 3D are explanative diagrams illustrating how to use the apparatus for cystographic inspection shown in FIG. 1.

First, a nozzle of syringe cylinder 26 filled with contrast medium is engaged into one end 24 of a catheter 12, and the catheter 12 having the chain 14 loaded therein is inserted into the urinary bladder 42 from an exterior urethral opening 40, as shown in FIG. 3A.

Figure 3B:
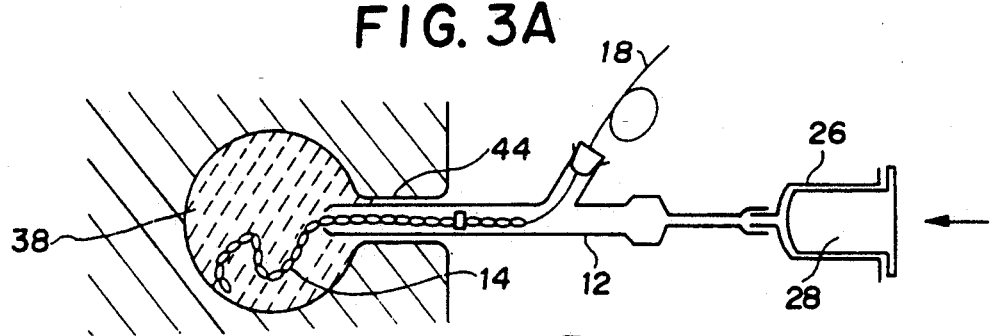

Then, as shown in FIG. 3B, piston 28 of the syringe is pushed forward to inject a contrast medium 38 into the catheter 12 and thereupon the chain 14 loaded in the catheter 12 is moved forward to break thin film 22a open and is emitted into the urinary bladder 42 at the same time as the injection of the contrast medium 38. After that, contrast medium 38 is injected up to the maximum micturition.

Figure 3C:
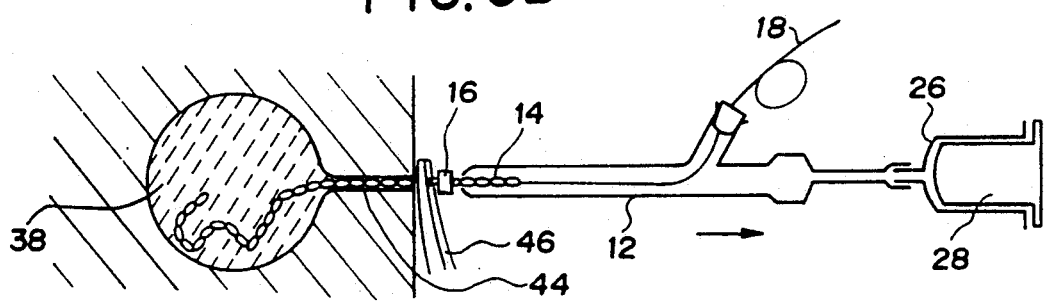

Then, the catheter 12 is pulled out of the urethra 44, the marker 16 is moved to the exterior urethral opening 40 with a pincette 46 as shown in FIG. 3C and in the situation of holding the chain 14 at the exterior urethral opening 40 with the pincetter 46, the catheter 12 is further moved back to pull the catheter 12 out of the urethra 44 leaving the string 18 intact. At this time, the inside diameter of the urethra contracts to the size of the outside diameter of the chain 14 from that of the outside diameter of the catheter 12.

Figure 3D:
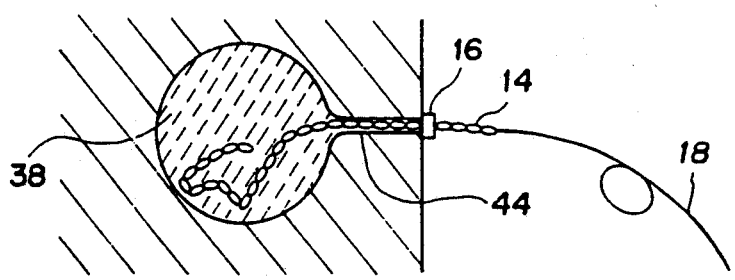

After the entire string 18 is pulled out of the catheter 12, only the chain 14 is left in the urethra 44 and the urinary bladder 42 as shown in FIG. 3D. That is, the chain 14 remains over the entire range extending from the exterior urethral opening 40 to the urethra 44 of the urinary bladder 42.

When roentgenographing is effected in this situation, images of the chain 14 and the urethra 44 extending from the exterior urethral opening 40 into the urinary bladder 42 can be observed and as the result, the flexed condition of the urethra and the posterourethrovesical angle can be clearly confirmed and measured. The position of the exterior urethral opening 40 can also be surely grasped by the image of the marker 16 disposed by the exterior urethral opening 40, and the mutual angle and positional relationships of such individual organs in the roentgenogram can be clearly observed, and hence a precise cystographic examination can be conducted.

As described above, according to the present invention, the flexed condition of the urethra extending from the exterior urethral opening to the urinary bladder 42 and the posterourethrovesical angle can be clearly confirmed by means of the urethral locus indicating member, and the position of the exterior urethral opening can be surely grasped by the marking member. Consequently, a precise cystographic examination can be achieved by the present invention.

While there has been described a preferred form of the invention, obviously modifications and variations are possible in light of the above teachings. It is therefore to be understood that within the scope of the appended claims, the invention may be practical otherwise than as specifically described.

What is claimed is:

1. An apparatus used for cystographic inspection for examining a flexed condition of the urethra and a posterourethrovesical angle, the apparatus comprising:

a catheter for insertion through the urethra into the urinary bladder of a patient, said catheter injecting a contrast medium into the urinary bladder and being drawn out of the urethra after an injection of the contrast medium has been completed;

said catheter including a housing;

a cylindrical injector for containing the contrast medium and removably-connected to one end of said housing;

a urethral locus indicating member removably positioned in said housing and including a chain formed such that it can be roentgenographed, said chain being emitted out of out of said housing through another end thereof into the urinary bladder at a front portion of said chain upon said injection of the contrast medium into the urinary bladder and being left in a region extending from the urethra to the urinary bladder after the catheter has been drawn out of the urethra; and a marker which is formed such that it can be roentgenographed, said marker being adjustably fixed on said chain in a predetermined position and at a distance from a front end of said chain and having a diameter larger than that of said urethral locus indicating member so as to prevent said marker from penetrating into the urethra when said chain is inserted into the urinary bladder and permit detection of the external urethral opening when said chain with said marker are roentgenographed.

2. The apparatus according to claim 1, wherein said housing comprises a polytetrafluoroethylene tube having a branched tube section formed at an intermediate portion of the tube, said urethral locus indicating member further including a string member connected to said chain and passing into said housing through said branched tube section for drawing said chain out of the urethra after completion of roentgenography.

3. The apparatus according to claim 1, wherein said chain is made of nickel plated brass and has a length of about 30 to 40 cm.

4. The apparatus according to claim 1, wherein said marker can slideably be moved on said chain for adjustment to be fixed thereon in said predetermined position.

5. The apparatus according to claim 1, wherein said marker includes a metal ring fitted into a periphery thereof.

6. The apparatus according to claim 1, wherein said urethral locus including member further includes a string member utilized to draw said chain out of the urethra after completion of roentgenography.

7. The apparatus according to claim 1, wherein said cylindrical injector has a pointed end portion for fitting into said one end of said housing of the catheter.

8. The apparatus according to claim 1, wherein said housing has at said another end thereof a thin film breakable by said chain when said chain is emitted out of said housing.

* * * * *